(12) United States Patent
Chenegros et al.

(10) Patent No.: US 11,185,337 B2
(45) Date of Patent: Nov. 30, 2021

(54) TOURNIQUET WITH ELASTIC SLEEVE (71) Applicants: SORBONNE UNIVERSITE, Paris (FR); CENTRE NATIONAL DE LA RECHERCHE SCIENTIFIQUE (CNRS), Paris (FR); INSTITUT NATIONAL DE LA SANTE ET DE LA RECHERCHE MEDICALE (INSERM), Paris (FR); FILIX, Creney (FR)

(72) Inventors: Guillaume Chenegros, Trappes (FR); Nicolas Libert, Paris (FR); Stephane Carras, Conde sur Noireau (FR)

(73) Assignees: SORBONNE UNIVERSITY, Paris (FR); CENTRE NATIONAL DE LA RECHERCHE SCIENTIFIQUE (CNRS), Paris (FR); INSTITUT NATIONAL DE LA SANTE ET DE LA RECHERCHE MEDICALE (INSERM) FILIX, Creney (FR)

( * ) Notice: Subject to any disclaimer, the term of this patent is extended or adjusted under 35 U.S.C. 154(b) by 44 days.

(21) Appl. No.: 16/486,672

(22) PCT Filed: Feb. 16, 2018

(86) PCT No.: PCT/EP2018/053869
§ 371 (c)(1),
(2) Date: Aug. 16, 2019

(87) PCT Pub. No.: WO2018/149958
PCT Pub. Date: Aug. 23, 2018

(65) Prior Publication Data
US 2020/0054345 A1 Feb. 20, 2020

(30) Foreign Application Priority Data
Feb. 17, 2017 (FR) ........................ 1751317

(51) Int. Cl.
*A61B 17/132* (2006.01)
(52) U.S. Cl.
CPC ................. *A61B 17/1322* (2013.01)
(58) Field of Classification Search
CPC . A61B 17/132; A61B 17/1322; A61B 17/135; A61B 2017/12018
See application file for complete search history.

(56) References Cited

U.S. PATENT DOCUMENTS 800,467 A * 9/1905 Myers ................... A61F 5/0585
602/5
814,795 A * 3/1906 Myers ..................... A61F 13/04
602/6

(Continued)

FOREIGN PATENT DOCUMENTS

FR    0858665 A    11/1940
WO    03/49623 A1   6/2003
WO    2015/001542 A1  1/2015

OTHER PUBLICATIONS

International Preliminary Reporton Patentability received for PCT Patent Application No. PCT/EP2018/053869, dated Aug. 29, 2019, 15 pages (8 pages of English Translation and 7 pages of Original Document).

(Continued)

*Primary Examiner* — Ryan J. Severson
(74) *Attorney, Agent, or Firm* — Womble Bond Dickinson (US) LLP (57) ABSTRACT

The present invention relates to a tourniquet (1) comprising:
• a support (2) for surrounding a first portion of a limb, • an elastic sleeve (4) to be held in a stretched position around the support (2), the support (2) preventing contraction of the elastic sleeve (4), • a grip element (8) which is movable relative to the support (2), • a drive element (6) for driving the elastic sleeve (4), when the grip element (8) is moved (Continued)

manually relative to the support (2), from its stretched position around the support to a blood vessel constricting position wherein the elastic sleeve (4) surrounds a second portion of the limb, adjacent to the first portion of the limb but not surrounded by the support (2), in such a way that the elastic sleeve (4) can contract by resilient return, and thus compress the second portion of the limb.

20 Claims, 7 Drawing Sheets

(56) References Cited

U.S. PATENT DOCUMENTS

| | | | | |
|---|---|---|---|---|
| 1,992,344 | A * | 2/1935 | Alhadate | A61F 15/005 |
| | | | | 602/63 |
| 2,333,237 | A * | 11/1943 | Erekson | A61B 17/1322 |
| | | | | 606/203 |
| 2,443,115 | A * | 6/1948 | Park | A47G 25/905 |
| | | | | 223/111 |
| 3,227,335 | A * | 1/1966 | Minnema | A47G 25/908 |
| | | | | 223/111 |
| 3,401,856 | A * | 9/1968 | Berlin | A47G 25/905 |
| | | | | 223/111 |
| 6,523,729 | B1 * | 2/2003 | Gardon-Mollard | |
| | | | | A47G 25/907 |
| | | | | 223/112 |
| 6,537,298 | B2 * | 3/2003 | Dedo | A61B 17/1322 |
| | | | | 606/203 |
| 7,326,227 | B2 * | 2/2008 | Dedo | A61B 17/1322 |
| | | | | 604/289 |
| 7,854,748 | B2 * | 12/2010 | Gavriely | A61F 13/08 |
| | | | | 606/203 |
| 8,366,739 | B2 * | 2/2013 | Gavriely | A61B 17/132 |
| | | | | 606/203 |
| 8,465,514 | B1 * | 6/2013 | Rose | A61B 17/1327 |
| | | | | 606/203 |
| 9,545,259 | B2 * | 1/2017 | Gavriely | A61B 17/1322 |
| 10,105,143 | B2 * | 10/2018 | Smith | A61B 17/12013 |
| 10,194,916 | B2 * | 2/2019 | Gavriely | A61B 17/1322 |
| 2003/0065357 | A1 | 4/2003 | Dedo et al. | |
| 2005/0080450 | A1 * | 4/2005 | Gavriely | A61B 17/1322 |
| | | | | 606/201 |
| 2009/0209891 | A1 * | 8/2009 | Gavriely | A61B 17/1322 |
| | | | | 601/134 |
| 2009/0254012 | A1 * | 10/2009 | Gavriely | A61B 17/132 |
| | | | | 601/134 |
| 2010/0100025 | A1 | 4/2010 | Kane | |
| 2012/0158041 | A1 * | 6/2012 | Craig | F41H 1/02 |
| | | | | 606/203 |
| 2014/0364873 | A1 * | 12/2014 | Smith | A61B 17/12013 |
| | | | | 606/140 |
| 2015/0342614 | A1 * | 12/2015 | Gavriely | A61B 17/1322 |
| | | | | 606/203 |
| 2016/0143647 | A1 * | 5/2016 | Gavriely | A61B 17/1322 |
| | | | | 606/203 |
| 2020/0054345 | A1 * | 2/2020 | Chenegros | A61B 17/1322 |

OTHER PUBLICATIONS

International Search Report and Written Opinion received for PCT Patent Application No. PCT/EP2018/053869, dated Apr. 12, 2018, 19 pages (9 pages of English Translation and 10 pages of Original Document).

Preliminary Research Report and Written Opinion received for French Application No. 1751317, dated Oct. 5, 2017, 8 pages (1 page of French Translation Cover Sheet and 7 pages of original document).

* cited by examiner

TOURNIQUET WITH ELASTIC SLEEVE

FIELD OF THE INVENTION

The present invention relates to a tourniquet.

A tourniquet is a device intended to interrupt the circulation of blood in a limb—upper limb (arm, forearm, hand) or lower limb (thigh, leg, foot)—by compressing the blood vessels of the limb using an element positioned around the limb.

PRIOR ART

Known from the prior art is a tourniquet called a "twist tourniquet," comprising a tensioning strap and a gripper bar. The strap surrounds a limb to be constricted, and the gripper bar is connected to the strap in such a way that rotation of the tensioning bar on itself has the effect of tightening the strap against the limb, which has the effect of compressing the blood vessels.

However, a twist tourniquet has the disadvantage of not being easily usable with only one hand.

In fact, a twist tourniquet requires a certain force to sufficiently tighten the strap so as to stop a hemorrhage. Yet an already injured person cannot always develop such a force.

Moreover, the strap can be tightened excessively around the arm when the gripper bar is turned on itself for too high a number of turns, and it is not easy to detect such an excessive tightening. Yet excessive tightening is likely to create tissue lesions in the constricted limb.

There exist moreover pneumatic tourniquets having an inflatable element. The compression of the limb to be constricted is exerted when the inflatable element, arranged around the limb, is inflated. However, these tourniquets have the disadvantage of being sensitive to variations of altitude: the compressions exerted by a pneumatic tourniquet on the same limb at two different altitudes are therefore not the same.

These pneumatic tourniquets are moreover complex to use. Their use is often reserved for qualified personnel. The result is that an unqualified person cannot easily place on himself a pneumatic tourniquet of this type.

DISCLOSURE OF THE INVENTION

One goal of the invention is to propose a tourniquet that is insensitive to variations of altitude that an injured person can easily apply to himself very rapidly.

Hence a tourniquet is proposed comprising:
  a support capable of surrounding a first portion of a limb,
  an elastic sleeve capable of being held in a stretched position around the support, the support preventing contraction of the elastic sleeve,
  a grip element movable with respect to the support,
  a drive element capable of driving the elastic sleeve when the grip element is displaced manually with respect to the support, from its stretched position around the support to a constricting position in which the elastic sleeve surrounds a second portion of the limb, adjacent to the first portion of the limb but not surrounded by the support, so that the elastic sleeve can contract by elastic return and thus compress the second portion of the limb.

When the elastic sleeve extends around the support, the support prevents the elastic sleeve from contracting. It is therefore possible to pre-position the tourniquet on a limb of a person as a preventive measure, without the elastic sleeve compressing this limb, and with a view to future use.

Once the support has been positioned around the first portion of the limb of a user, and if perchance this user came to be injured in such a manner that the second portion of this limb needs to be constricted, it is then sufficient for him to seize the grip element and to displace it with respect to the support, so that the elastic sleeve is driven, by means of the driving element, off the support which has holding it in a stretched state until it reaches the second portion of the limb to be constricted. As the second portion of the limb is not surrounded by the support, the elastic sleeve, previously in a stretched state, is free to contract to compress the blood vessels of the second portion of the limb.

Once pre-positioned on the limb, this tourniquet is thus very simple to trigger, particularly by and on a wearer of the tourniquet.

Moreover, as compression of the blood vessels is ensured by the elastic sleeve, the proposed tourniquet is not sensitive to variations of altitude as is the case for existing tourniquets of the pneumatic type.

The tourniquet according to the present invention can also comprise the following optional features, taken alone or in combination when that is technically possible.

The drive element can comprise a first portion and be capable of adopting:
  a folded configuration in which the first portion extends between the support and the elastic sleeve held in the stretched position around the support,
  a deployed configuration in which the elastic sleeve, in its constricting position, extends between the first portion and the second portion of the limb when the support surrounds the first portion of the limb.

In this case, the grip element is arranged with respect to the first portion so that a displacement of the grip element with respect to the support shifts the first portion of the grip element from the folded configuration to the deployed configuration so as to displace, by lever action, the elastic sleeve from the stretched position to the constricting position.

The first portion can be suitable for:
  in the folded configuration, surrounding the support so that the elastic sleeve held in the stretched position extends around the first portion,
  in the deployed configuration, surrounding the elastic sleeve.

The first portion can also be capable of taking on an annular shape extending around an axis in the deployed configuration, and is manufacture in a material that is non-extendable parallel to the axis.

The drive element can comprise a second portion continuing the first portion. In this case, in the folded configuration, the second portion is folded over the first portion so as to form, between the first and the second portion of the drive element, a cavity for housing the elastic sleeve held in the stretched position.

The tourniquet can comprise means for locking the second portion of the drive element in the folded configuration on the first portion of the drive element.

The locking means can comprise:
  at least one opening formed in the first portion,
  at least one opening formed in the second portion,
  a cord capable of being passed through the two openings, the cord having a free end portion capable of being accessible from the outside of the tourniquet and to be pulled manually to withdraw the cord from the openings, so as to unlock the two portions from one another.

The openings can be disposed with respect to one another so that a portion of the cord extending from one of the openings to the other opening forms an abutment preventing the elastic sleeve housed in the cavity from leaving the cavity.

The drive element can comprise a third portion which continues the second portion and which furthermore is fastened to the grip element, the second portion then extending between the elastic sleeve and the third portion in the folded configuration.

The displacement of the grip element inducing the driving, by the drive element, of the elastic sleeve from the stretched position around the elastic sleeve to the constricting position can be a displacement caused by manual pulling exerted on the drive element along the limb.

The grip element can comprise a fastening element capable of fastening the grip element removably to a piece of clothing while the elastic sleeve is held around the support in its stretched position, and the grip element is fastened to the drive element to prevent, when the grip element is fastened to a piece of clothing, the driving by the drive element of the elastic sleeve from its stretched position around the support to its constricting position.

The fastening element is for example capable of forming, with another fastening element, a hook-and-pile connection.

The fastening element can be capable of fastening the grip element on a portion of a piece of clothing surrounding a third portion of the limb when the support surrounds the first portion of the limb, the second and third portions of the limb being situated on either side of the first portion of the limb.

The grip element can comprise a flap that is movable with respect to the drive element between:
  an unfolded configuration in which the fastening element faces the piece of clothing, so as to be able to be attached to the piece of clothing,
  a configuration folded back on the drive element in the direction of the constricting position.

The support can have an internal surface capable of being oriented toward the first portion of the limb, and an external surface opposite to the internal surface, and the tourniquet can also comprise:
  an internal textile element covering the internal surface, and/or
  an external textile element covering the external surface.

The two textile elements can together define a pocket for containing the support, the pocket being provided with an opening through which the support is capable of being withdrawn from the pocket.

The tourniquet can also comprise means for blocking the opening of the pocket, such as a zipper.

At least one of the textile elements can be formed from a strip having two opposite free edges brought to face one another without overlapping them, and sewn together by means of a topstitch.

the strip can have the shape of a parallelogram.

At rest, the elastic sleeve can have an annular shape extending around an axis, and comprise at least one elastic compression yarn arranged so as to follow a substantially helical trajectory around and along the axis.

According to another aspect of the invention, a piece of clothing or a portion of a piece of clothing is also proposed, such as a sleeve or a trouser leg, comprising at least one tourniquet conforming to the description above.

DESCRIPTION OF THE FIGURES

Other features, aims and advantages of the invention will be revealed by the description that follows, which is purely illustrative and not limiting, and which must be read with reference to the appended drawings in which.

In all the figures, similar element bear identical reference symbols.

DETAILED DESCRIPTION OF THE INVENTION

Illustrated in the appended figures is a tourniquet 1 comprising a support 2, an elastic sleeve 4, a drive element 6 and a grip element 8 movable with respect to the support 2.

Figure 1:
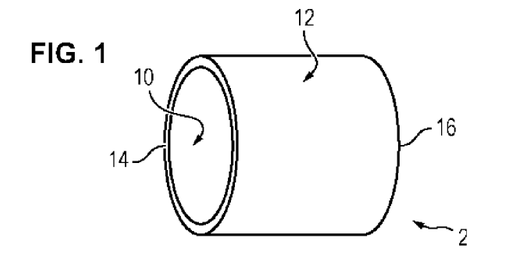
FIG. 1 is a perspective side view of a support forming part of a tourniquet, according to one embodiment.

With reference to FIG. 1, the support 2 is capable of surrounding a limb—upper limb (arm, forearm, hand) or lower limb—(thigh, leg, foot) of a wearer.

The support 2 comprises or consists of a tube made of plastic (such as polypropylene), or of carbon. The support is generally manufactured of a material preventing contraction of the elastic sleeve 4, which will be described below.

The support 2 can have a cylindrical shape and/or axially symmetrical shape. Alternatively, the tube made of plastic can have a more complex shape, substantially complementary to a bare limb or to a limb surrounded by clothing.

The support 2 has an internal surface 10 intended to be oriented toward a limb of the wearer, and an external surface 12 opposite to the internal surface, a first edge 14 and a second edge 16 opposite to the first edge 14, the two edges 14, 16 each connecting the internal surface 10 to the external surface 12.

For example, the rigid support 2 has an internal diameter of 118 millimeters (+/−1 mm), and has a radial thickness of 3 millimeters (+/−0.2 millimeters) measured between its internal surface 10 and its external surface 12, and has a width, measured between the two edges 14 and 16, of 40 millimeters (+/−0.1 millimeters).

With reference to FIGS. 2 to 5, the tourniquet 1 also comprises an internal textile element 18 and an external textile element 20.

The internal textile element 18 is designed to cover the internal surface 10 of the rigid support 2. Thus the rigid support 2 cannot enter directly into contact with the skin of the limb. In particular, when the rigid support 2 is made of plastic, this plastic is capable of causing skin allergies; the internal textile element allows such allergies to be avoided in this case.

Figure 2:
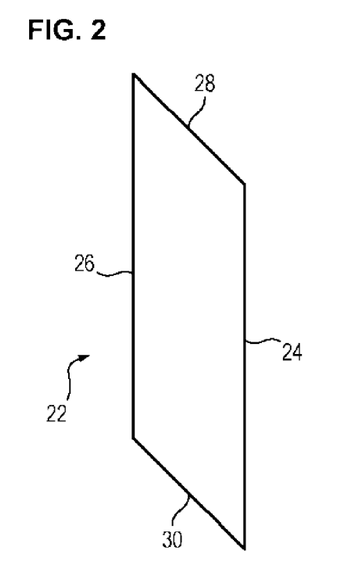
FIGS. 2 to 5 are views showing top views or perspective side views of two textile elements also forming part of a tourniquet, according to one embodiment.

The internal textile element 18 is manufacture starting with a first strip of material 22 preferably having the shape of a parallelogram. The two long opposite sides 24, 26 of the first strip 22 are each for example 370 millimeters in length and the two short opposite sides 28, 30 of the first strip 22 are each for example 37 millimeters in length. The internal textile element 18 has for example a thickness of 1 to 2 millimeters.

The two short sides 28, 30 are connected to one another without overlapping, by means of a topstitch 32. Such a connection has the advantage of being particularly comfortable for the wearer of the tourniquet 1, because it does not create excess thickness. Moreover, the parallelogram shape of the strip 22 allows a topstitch 32 of greater length to be applied than if the strip has been of rectangular shape, which makes this connection comparatively more durable.

Figure 3:
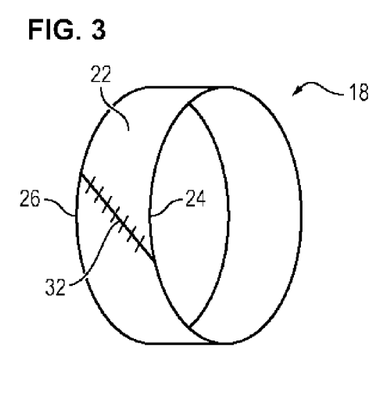

Thus closed over itself, the internal textile element 18 has an annular shape, as can be seen in FIG. 3.

The internal textile element 18 is ideally made of water-repellent flame-proof polyether sulfone (PES), or of water-repellent polyamide (PA) of the 100% cordura type or others with flame-proof treatments. Furthermore, it has a weight of 120 to 450 g/m$^2$. The internal textile element 18 also comprises a weave of the plain type, of the twill type or any other type of weave.

Figure 4:
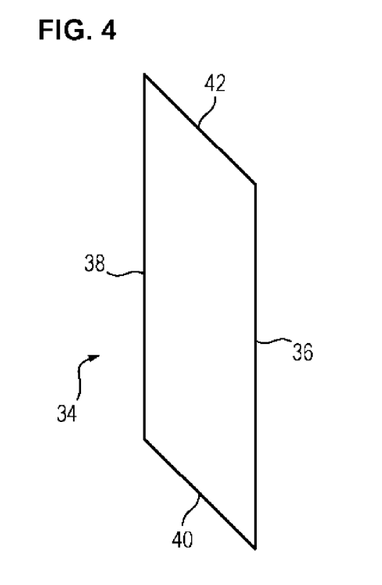
Figure 5:
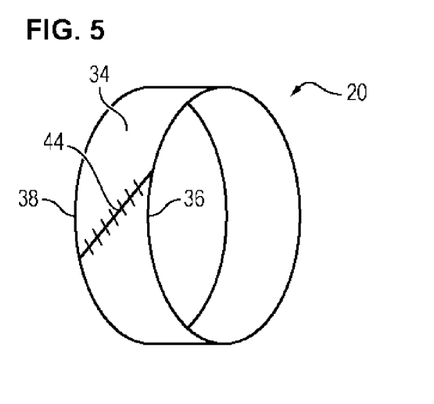

Furthermore, the external textile element 20 is intended to cover the external surface 12 of the rigid support 2.

The external textile element 20 is manufacture starting from a second strip of material 34, preferably with a parallelepiped shape. The two long opposite sides 38, 40 of the second strip are each for example 370 millimeters long and the two short opposite sides 40, 42 of the second strip are each for example 35 millimeters long. The external textile element 20 has a thickness of 1 to 2 millimeters.

As for the internal textile element 18, the two short sides 40, 42 of the second strip 34 are connected to one another without overlapping, by means of a topstitch. This has the advantage of avoiding any undesirable excess thickness.

The external textile element 20 is preferably rigid (along a warp direction and a fill direction). The external textile element 20 can be manufactured in a material identical to the material of the internal textile element 18. Alternatively, the external textile element 20 can be manufactured based on polyurethane and polyether sulfones (PES) or polyamide (PA), in of a rubber obtained by vulcanizing Hevea. All the other properties mentioned above for the internal textile element 18 (weight, water-repellent nature, type of weave) are also applicable to the external textile element 20.

At least one of the textile elements 18, 20 can have slip-resistant yarns on one of its two faces (not illustrated in the figures), this face being intended to rest against one of the internal 10 or external 12 surface of the support 2, as the case may be. Thanks to these slip-resistant yarns, rotation of the support 2 relative to the textile element comprising such slip-resistant yarns can be prevented. Such rotation is undesirable when the support has a shape which is not axially symmetrical, because it would be able to hamper the wearer of the tourniquet 1.

Figure 6:
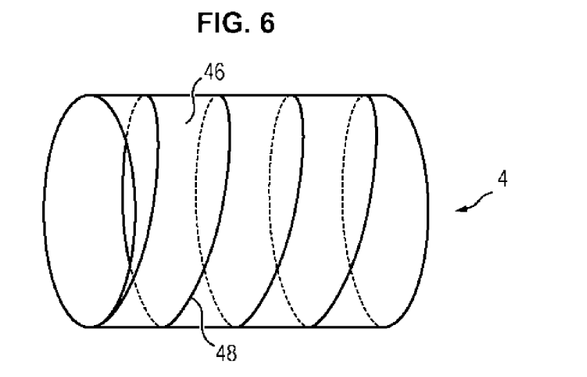
FIG. 6 is a perspective side view of an elastic sleeve forming part of a tourniquet, according to one embodiment.

With reference to FIG. 6, the elastic sleeve 4 is designed to be positioned around a limb in a stretched state, and to contract, by elastic return, toward the blood vessels of this limb, so as to interrupt a hemorrhage.

The elastic sleeve 4 is manufactured for example starting from an elastic strip closed over itself so as to assume, at rest, the shape of a tube. The elastic sleeve 4 is capable of being radially stretched, i.e. its diameter can be increased.

Typically, the elastic band from which the elastic sleeve is formed has, at rest, a length of 20 centimeters and a width of 10 centimeters. Its weight is preferably comprised between 15 and 25 grams.

The elastic sleeve 4 comprises a knitted fabric 46, consisting for example of a cladding yarn. The cladding yarn is for example made of polyamide.

The elastic sleeve 4 also comprises at least one elastic compression yarn 48. The elastic compression yarn 48 is interlaced with the knitted fabric 46 so as to follow a substantially helical trajectory around the axis of the tube formed by the elastic sleeve 4. One advantage of this type of shape of elastic compression yarn is that, even if it is broken when the elastic sleeve 4 is in a radially stretched state, it can still contract, by elastic return, to its contracted configuration, in a relatively uniform manner. In fact, breakage of the compression yarn creates two or more disjoint helical portions, each portion remaining retractable. The elastic compression yarn 48 comprises for example 20 to 40% spandex and 80 to 60% polyamide.

Moreover, the drive element 6 has as its function to drive the elastic sleeve 4, when the grip element 8 is displaced manually with respect to the support 2, from a stretched position around the support 2 to a constricting position in which the elastic sleeve 4 surrounds a second portion of the limb adjacent to the first portion of the limb but not surrounded by the support 2, so that the elastic sleeve can contract by elastic return and thus compress the second portion of the limb.

Figure 7:
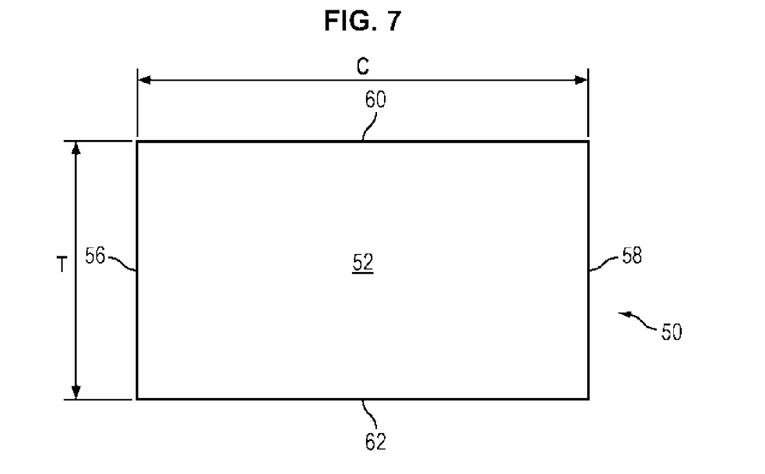
FIGS. 7 to 9 are top and side view of a drive element forming part of a tourniquet, according to one embodiment.
Figure 8:
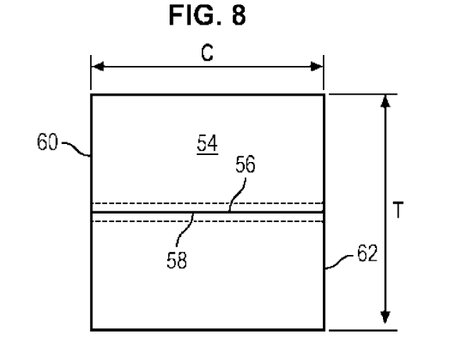
Figure 9:
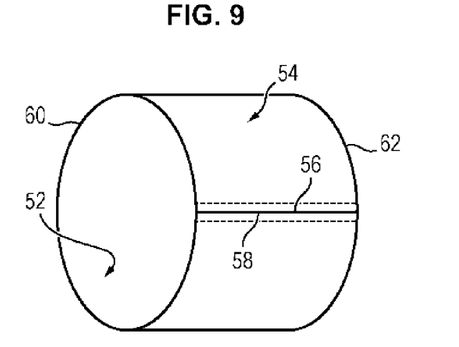

With reference to FIGS. 7 to 9, the drive element 6 of the tourniquet 1 is manufactured starting with a strip 50 called hereafter "drive strip" to distinguish it from the strips from which the internal 18 and external 20 textile elements are made.

The drive strip 50 comprises:
- a first surface 52, a second surface 54 opposite to the first surface 52,
- a first edge 56 and a second edge 58 opposite to the first edge 56, the two edges 56, 58 connecting the first surface 52 to the second surface 54, and each extending parallel to a fill direction T of the strip 50,
- a third edge 60 and a fourth edge 62 opposite to the third edge, the two edges also connecting the first surface to the second surface, and extending parallel to a warp direction C of the strip perpendicular to the fill direction T.

The drive strip 50, rectangular for example, has a length, measured parallel to the warp direction C, of 35 centimeters, and a width, measured parallel to the fill direction T, of 25 centimeters.

The drive strip 50 is ideally manufactured in a 2/1 twill fabric Z, possibly of taffeta or of any other type of weave. Preferably, its weight is comprised between 90 and 380 g/m$^2$.

The drive strip; 50 is extendable parallel to the fill direction T (i.e. the first edge 56 and the second edge 58 can be moved away from one another), but non-extendable in the warp direction C (i.e. the third edge 60 and the fourth edge 62 cannot be moved away from one another).

Preferably, the drive strip 50 comprises 2 to 8% spandex and 98 to 92% polyamide of the water-repellent cordura type with flame-proof treatment, or water-resistant flame-proofed polyester. Alternatively, the drive strip 50 is made of aramid fibers, such as poly(p-phenylene terephthalamide) (PPD-T) (known under the commercial designation Kevlar) a material that is advantageous for its durability, or of natural fibers such as flax.

To form the drive element 6, the edges 56, 58 of the drive strip 50 are positioned facing one another without overlapping, and are connected together by means of a topstitch. The drive element 6 thus has an annular shape having a diameter of approximately 17 cm (+/−0.5 cm), as shown in FIG. 9.

The warp direction C is parallel to an axis around which the drive element 6 extends in its annular configuration. Thus, the drive element 6 is not extendable parallel to this axis.

By convention, the configuration of the drive element 6 in which it has such an annular shape is called the "deployed configuration"; the drive element 6 can be deformed so as to adopt other configurations. In fact, as the drive strip 50 is extendable parallel to the fill T, the annular drive element 6 can be hemmed over itself one or more times around its axis, as will be seen hereafter.

Figure 10:
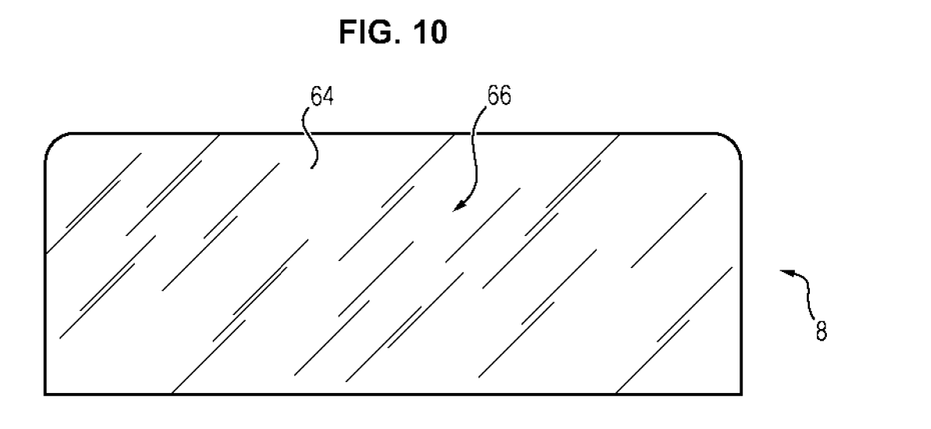
FIGS. 10 and 11 are top and bottom views of a grip element forming part of a tourniquet, according to one embodiment.
Figure 11:
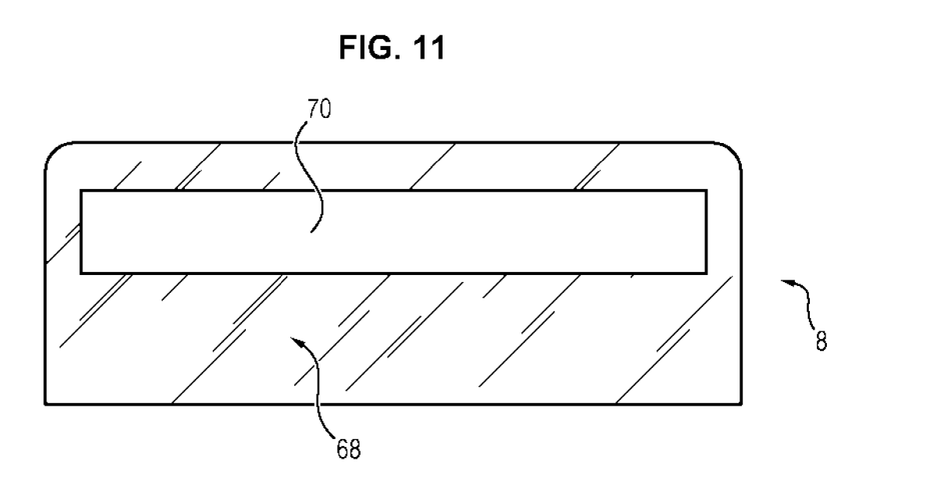

With reference to FIGS. 10 and 11, the grip element 8 comprises a flap 64, substantially rectangular for example. The flap 64 has two opposite surfaces 66, 68 (one being visible in FIG. 10 and the other in FIG. 11).

The flap 64 has for example a length of 11 cm and a width of 4 cm.

The flap 64 is preferably made of a textile laminated flexible plastic material, or of a coated or double-sided coated textile. Very preferably, the flap 64 is a flame-proof water-repellent article made of 100% polyester.

The grip element 8 comprises, on one of its two faces, a fastening element 70 capable of being fastened removably to a piece of clothing.

Typically, the fastening element 70 vis a strip of pile or of hooks designed to form, with a complementary fastening element attached to the piece of clothing, a hook-and-pile connection.

The fastening element 70 is for example rectangular and is for example 1 cm in width and 9 cm in length.

Figure 12:
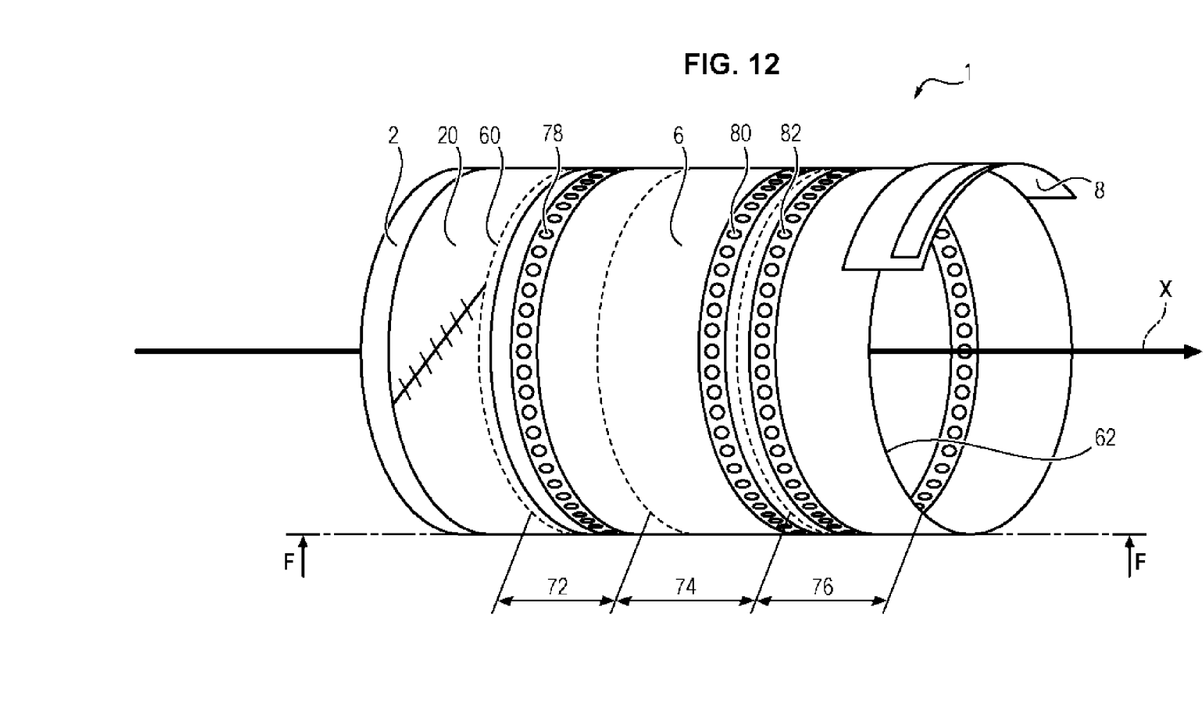
FIG. 12 is a lateral perspective view of a tourniquet according to a first embodiment, comprising the elements shown in the preceding figures.
Figure 13:
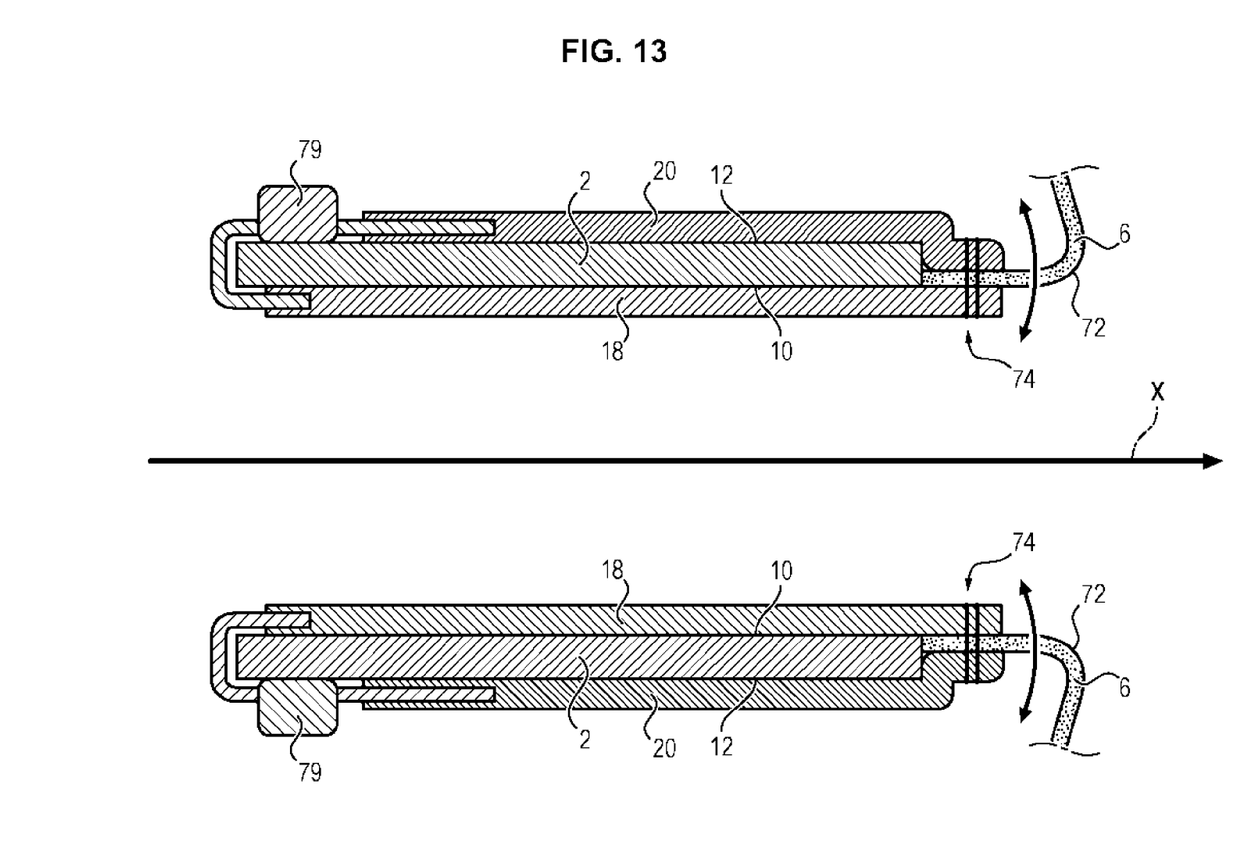
FIG. 13 is a partial longitudinal section view of the tourniquet shown in FIG. 12.
Figure 14:
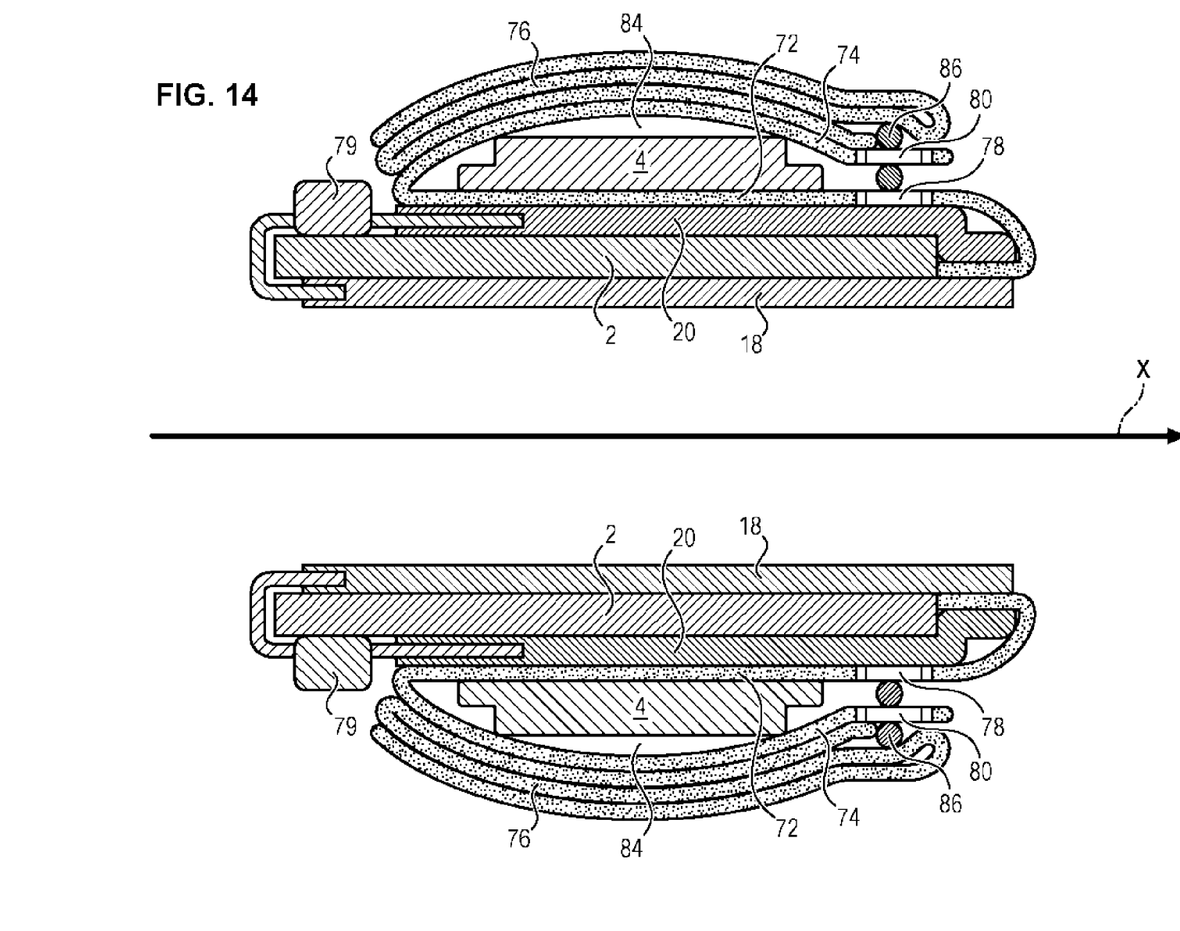
FIG. 14 is a longitudinal section view of the tourniquet shown in FIG. 12, in a folded configuration.

With reference to FIGS. 12 to 14, the two textile elements 18 and 20, the support 2, the elastic sleeve 4, the drive element 6 and the grip element 8 are assembled in the following manner to form the tourniquet 1.

The textile elements 18 and 20, the support 2, the elastic sleeve 4 and the drive element 6 are arranged coaxially, around an axis X.

The drive element 6 comprises successively, from the edge 60 to the edge 62 opposite to it: a first portion 72, a second portion 74 and a third portion 76. In FIG. 12, the two junctions between portions 72 and 74 and between portions 74 and 76 are shown by two dotted lines. It will be seen hereafter that these portions have different functions.

The first portion 72 comprises a first plurality of openings 78, the second portion 74 comprises a second plurality of openings 80, and the third portion 76 comprises a third plurality of openings 82.

Each opening 78, 80, 82 leads into the two opposite surface 52, 54 of the drive element 6.

The openings of each plurality of openings 78, 80, 82 are distributed around the axis X of the drive element 6 when it is in its deployed configuration, in which it has an annular shape. The three pluralities of openings 78, 80, 82 extend in respective parallel planes, at a distance from one another along the axis of the drive element 6. It will be seen hereafter that a cord 86 is intended to be passed through the openings 78, 80, 82. To avoid tearing of the drive element 6 caused by friction of such a cord 86 against the edge of one of the openings, at least one of the openings 78, 80, 82 (all of them, for example) is provided with an eyelet.

The external textile element 20 is positioned around the internal textile element 18. They are fastened to one another by means of seams 74. An annular pocket is thus formed between the two textile elements 18, 20. Preferably, the first portion 72 of the drive element 6 is sandwiched between the two textile elements 18 and 20; the first portion 72 and the two textile elements, thus superimposed, are sewn together by means of seams 74.

The support 2 is inserted into the pocket formed between the two, internal and external, textile elements. The edge 60 of the drive element 6, confined between the two textile elements 18 and 20, participates in defining the pocket and is consequently located facing the support 2 housed in the pocket.

Preferably, the annular pocket has an annular opening allowing the withdrawal of the support housed in the pocket, or the insertion of a support into the pocket when it is empty. It is thus possible to replace a support 2 that is used, damaged or having an unsuitable shape with another support 2.

The annular opening of the pocket is located opposite the edge 60 of the drive element 6, with respect to the support 2 housed in the pocket.

The tourniquet 1 comprises blocking means 79 for blocking the opening of the pocket, such as a zipper. The opening of the pocket is blocked by means of the blocking means 79.

It should be noted that the external textile element 20 does not totally cover the internal textile element 18. The internal textile element has a width, measured parallel to the axis X, that is greater than the width of the external textile element, so that an end portion of the internal textile element is not covered by the external textile element 20. The blocking means are arranged facing this non-covered end portion. Once inserted into the pocket, the support thus being located between, on the one hand, the blocking means and the external textile element 20, and on the other hand the internal textile element 18.

Moreover, the grip element 8 is attached to the drive element 6 at its edge 62. More precisely, the flap 64 is sewn to the surface 54 of the drive element 6, at its third portion 76.

Thus, when the drive element 6 is in its deployed configuration in which it has an annular shape, the drive element 6 extends between the support 2 and the grip element 8. Moreover, in this same configuration, the surface 54 is oriented radially toward the exterior, and the opposite surface 52 oriented toward the interior of the drive element 6 with an annular shape.

The drive element 6 then undergoes the following deformations, made possible by its characteristic of being extendable in the fill direction T.

The drive element 6 is hemmed 180 degrees over itself by radial deformation of the drive strip 50 toward the exterior, so that the first portion 72 is folded around the support 2 (therefore against the external textile element 20 which surrounds the support 2).

The elastic sleeve 4 is positioned around the support 2 in a stretched state.

More precisely, the elastic sleeve 4 is positioned around and against the surface 52 of the first portion 72 of the drive element 6 folded around the support 2.

Of course, the elastic sleeve 4 has, at rest, a smaller diameter than the outside diameter of the first portion 72 of the drive element 6 folded around the support 2, so that the sleeve is in a stretched state when it is positioned around the first portion 72.

The drive element 6 is then again hemmed over itself a second time at the junction between the first portion 72 and the second portion 74.

More precisely, the second portion 74 is folded 180 degrees around the first portion 72, by radial deformation of the drive band 50 toward the exterior, so that the second portion 74 covers the elastic sleeve 4 stretched around the first portion 72.

The first portion 72 and the second portion 74 together define a cavity 84, visible in FIG. 14, having a substantially U-shaped profile of which the bottom corresponds to the junction between the first portion 72 and the second portion 74 of the drive element 6. In a configuration of this type, the elastic sleeve is thus protected against external attacks on the tourniquet 1 (caused for example by projectiles or bad weather).

The second portion 74 is folded around the first portion 72 so that at least one opening 80 formed in the second portion 74 is located facing an opening 78 formed in the first portion.

At least one pair of openings 78, 80 is arranged so that the elastic sleeve 4 housed in the cavity 84 is located between the two openings and the bottom of the cavity 84 formed by the junction between the first portion 72 and the second portion 74 of the drive element 6.

The drive element 6 is then again hemmed over itself a third time, at the junction between the second portion 74 and the third portion 76.

More precisely, the third portion 76 is folded 180 degrees radially toward the exterior around the second portion 74, by deformation of the drive band 50, so as to form a supplementary layer of protection of the elastic sleeve 4 housed in the cavity 84.

The third portion 76 is folded around the second portion 74 so that at least one opening 82 formed in the third portion 76 is located facing an opening 80 formed it the second portion 74.

Very preferably, the third portion 76 is folded around the second portion 74 so that all three, at least one opening 82 formed in the third portion 76, at least one opening 80 formed in the second portion 74, and an opening 78 formed in the first portion 72, are aligned.

The tourniquet 1 also comprises a cord having a grippable end portion, comprising for example a loop inside which a finger can be passed.

The cord 86 is passed through at least one of the openings formed in the first portion 72, through at least one of the openings formed in the second portion 74, perhaps through at least one of the openings formed in the third portion 76. Furthermore, it is arranged that the grippable end of the cord 86 is accessible from the exterior of the tourniquet 1, so as to be able to be gripped and pulled by a user.

The openings 78, 80 and the cord 86 thus form the locking means of the second portion 74 of the drive element 6 in its configuration folded over the first portion 72 of the drive element 6.

The openings 80, 82 and the cord 86 also form locking means of the third portion 76 of the drive element 6 in its configuration folded over the second portion 74 of the drive element 6. It should be noted that that FIG. 14 is not at the same scale as FIG. 12. The portion 76 shown in FIG. 14 has a length at least equal to the cumulative length of the portions 72 and 74.

The cord 86 is passed through at least one pair of openings 78, 80 formed respectively in the first portion 72 and the second portion 74 so that the elastic sleeve 4 housed in the cavity 84 is located between the two openings and the bottom of the cavity 84. The portion of the cord 86 extending from one of these two openings 78, 80 until the other opening 78, 80 thus forms an abutment preventing the elastic sleeve 4 housed in the cavity 84 from leaving it.

Thus, the cord 86 not only has the effect of preventing a deployment of the drive element to its deployed configuration shown in FIG. 12, but also the effect of preventing an untimely departure of the elastic sleeve 4 from the cavity 84 even when the second portion 74 is folded around the first portion 72 of the drive element 6, as illustrated in FIG. 14.

The assembly of the different parts of the tourniquet 1 is then completed. At this stage, the tourniquet is ready to be fastened to a piece of clothing.

Pre-Installation of the Tourniquet 1 on a Piece of Clothing

The tourniquet 1 is positioned on a piece of clothing, or a portion of a piece of clothing, in such a manner that the support 2 surrounds a portion of the piece of clothing intended to surround a limb: this portion is therefore for example a sleeve or a trouser leg.

In a first variant, the textile element 18 rests against an exterior surface of this portion of a piece of clothing, and perhaps is sewn to it. In a second variant, the internal textile element 18 of the tourniquet 1 itself forms a part of the portion of a piece of clothing.

The portion of the piece of clothing comprises three successive portions: a proximal portion (intended to be near a shoulder in the case of a sleeve), an intermediate portion continuing the proximal portion, and a distal portion (designed to be closer to a hand in the case of a sleeve) continuing the intermediate portion.

The tourniquet 1 is positioned so that the support 2 extends around the intermediate portion of the portion of the piece of clothing. The proximal portion and the distal portion of the portion of the piece of clothing are not covered by the support 2, but are situated on either side of it.

The sleeve comprises, on the external surface of its proximal portion, a second fastening element adapted to cooperate with the fastening element 70 of the grip element 8 of the tourniquet 1. The second fastening element is for example a hook strip when the fastening element 70 is a pile strip, or vice versa.

The grip element 8 of the tourniquet 1 overlies the exterior surface of the proximal portion of the portion of the piece of clothing. The two fastening element are positioned against one another, together forming for example a hook-and-pile type connection.

A user can then put on the piece of clothing comprising the portion of the piece of clothing around which the tourniquet 1 has thus been pre-positioned.

For example, when the portion of the piece of clothing is a sleeve, and once the user has put on the piece of clothing comprising such a sleeve, the sleeves surrounds an arm of this user. For example, the proximal portion of the sleeve surrounds a proximal segment of an arm, the intermediate portion surrounds an intermediate segment of the arm, and the distal portion surrounds a distal portion of the arm.

Of course, several tourniquets can be pre-positioned on the same piece of clothing, four for example (two for the arms and two for the legs).

Use of the Tourniquet by a Wearer of the Tourniquet

Let us now imagine that the wearer of the tourniquet suffers and injury such that it is necessary to compress by restriction the blood vessels of the distal segment of his arm. The zone to be compressed is therefore the exterior surface of the distal segment of the arm. The wearer is wearing a tourniquet 1 on the sleeve surrounding the injured arm.

With his other, uninjured, arm, the wearer seizes the flap 64 of the grip element 8 and moves it away from his injured arm so that the fastening element 70 and the second fastening element are detached from one another.

At this stage, it is not yet possible to displace the elastic sleeve 4 toward the zone to be constricted with respect to the support 2 around which it extends in a stretched state, due to the locking means formed by the cord 86 passing through the openings 78, 80, 82.

Thus, the wearer seizes the free end portion of the cord 86, accessible from the exterior of the tourniquet 1. By pulling on this cord 86, the cord 86 unwinds out of the openings 78, 80, 82, which has the effect not only of opening the cavity 84 in which the elastic sleeve 4 is housed, defined between the first portion 72 and the second portion 74 of the drive element 6, but also allowing displacement of the first portion 72 and of the second portion 74 along the limb, toward the zone to be constricted.

The wearer folds the flap 64 180 degrees toward the zone to be constricted, and pulls the flap 64 thus folded toward the zone to be constricted. The flap 64 being fastened to the drive element 6, this pull has the effect of driving the third portion 76 toward the zone to be constricted. During this displacement, the third portion 76 shifts from its configuration folded around the second portion 74 to a deployed configuration in which it overlies the zone to be constricted.

By continuing this same pulling movement, the first portion 72 of the drive element 6 shifts 180 degrees from its folded configuration to its deployed configuration and drives, by lever action, the elastic sleeve 4 resting on the first portion 72 to a constricting position overlying the zone to be constricted. This lever action is advantageous because the elastic sleeve can be displaced by means of a relatively weak pulling force. In this manner, a user is capable of exerting this pull even when he is injured.

Moreover, due to the fact that the first portion 72 of the drive element 6 extends around the support 2, the lever action is applied by the first portion 72 of the drive element 6 over the entire circumference of the stretched elastic sleeve 4 that surround it. In this manner, the risks of breaking the elastic sleeve 4 during shifting of the first portion 72 from its folded position to its deployed position are reduced.

Moreover, the fact that the first portion 72, and more generally the drive element 6, are non-extendable parallel to the axis X allows it to implement a more effective movement transmission from the pulled grip element 8 to the elastic sleeve 4.

Once the first portion 72 is deployed, the elastic sleeve finds itself in its constricting position, around the zone to be constricted. The first portion 72 then surrounds the elastic sleeve 4 between the first portion 72 and the zone to be constricted.

As the elastic sleeve 4 is not held, in its constricting position, in a stretched state by the support 2, the elastic sleeve 4 contracts freely by elastic return and thus compresses the zone to be constricted which it surrounds.

The invention is not limited to the embodiment described previously, but can also be the object of many other variants.

For example, in the embodiment previously described, it was considered that the internal textile element 18 formed a part of the piece of clothing or was sewn to it, and that the fastening element of the flap 64 cooperated with a fastening element forming a part of the piece of clothing, sewn to it for example.

Figure 15:
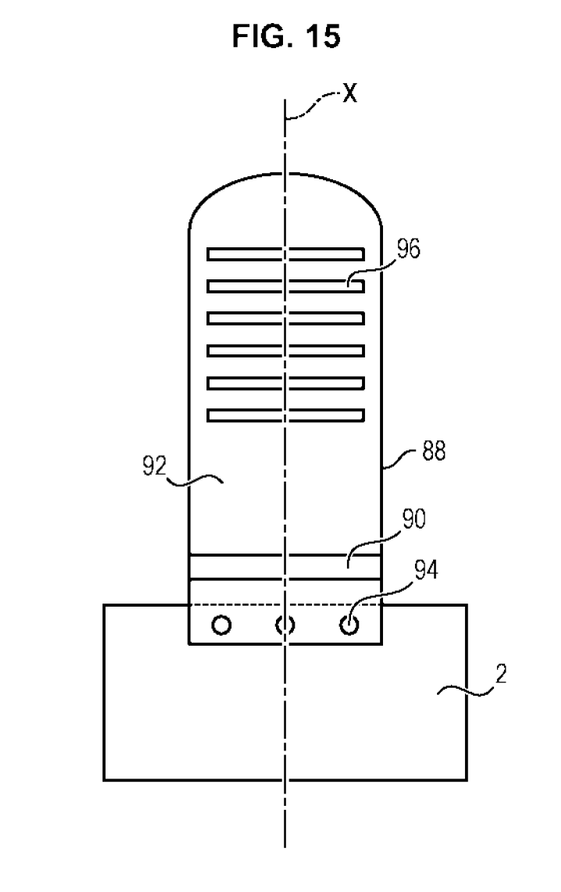
FIGS. 15 and 16 are two top views of a support element forming part of a tourniquet according to a second embodiment.

In another embodiment, the tourniquet 1 comprises and addition support element 88 to support the second fastening element which cooperates with the fastening element 70 of the grip element 8.

With reference to FIG. 15, the support element 88 appears in the form of a support strip intended to extend along a sleeve. In this figure, the second fastening element is labeled 90. This second fastening element 90 is fastened on an external surface of the support element 88.

The support element 88 is fastened to the support 2, for example via rivets 94.

The support element 88 also has an internal surface intended to be oriented toward the sleeve and an external surface opposite to the internal surface on which is arranged the fastening element.

Moreover the support element has a plurality of parallel slots 96. The slots 96 extend transversely to the axis X around which the support 2 extends. When the tourniquet 1 is mounted on an arm, an epaulette of the piece of clothing can be passed through one of the slots 96 and closed over itself. Thus, the support strip extends over the proximal portion of the arm between the epaulette and the support 2.

Figure 16:
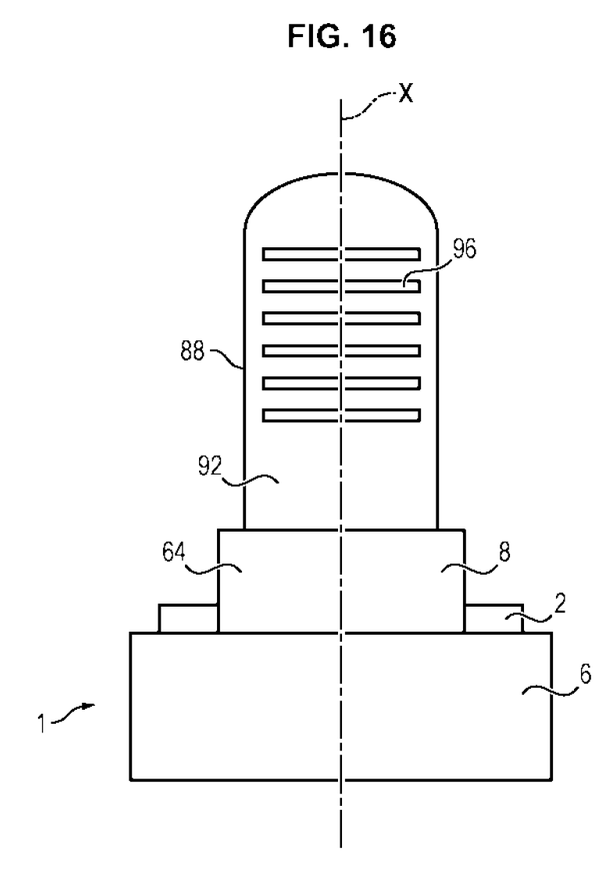

With reference to FIG. 16, the flap 64 of the grip element 8 overlies the support element 88 and the other fastening element arranged on its exterior surface. Thus, rather than fixing the flap 64 directly to the piece of clothing, the flap 64 is fixed to the additional support element, which is advantageous when it is not possible to sew the fastening element to the piece of clothing.

Moreover, the fact of providing several parallel slots 96 allows adapting the placing of the support strip to several sizes of forearms.

The invention claimed is:

1. A tourniquet comprising:
a support capable of surrounding a first portion of a limb,
an elastic sleeve capable of being held in a stretched position around the support, preventing a contraction of the elastic sleeve,
a grip element movable with respect to the support,
a drive element capable of driving the elastic sleeve, when the grip element is manually displaced with respect to the support, from the stretched position around the support to a constricting position in which the elastic sleeve surrounds a second portion of the limb adjacent to the first portion of the limb but not surrounded by the support, so that the elastic sleeve can retract itself by elastic return, and thus compress the second portion of the limb,
wherein the drive element comprises a first portion and is capable of adopting:
a folded configuration wherein the first portion extends between the support and the elastic sleeve maintained in the stretched position around the support,
a deployed configuration wherein the elastic sleeve, in the constricting position, extends between the first portion and the second portion of the limb when the support surrounds the first portion of the limb,
and wherein the grip element is arranged with respect to the first portion so that a displacement of the grip element with respect to the support causes the first portion of the drive element to shift from the folded configuration to the deployed configuration so as to displace, by lever action, the elastic sleeve from the stretched position to the constricting position.

2. The tourniquet according to claim 1, wherein the first portion is capable of:
in the folded configuration, surrounding the support so that the elastic sleeve held in the stretched position extends around the first portion,
in the deployed configuration, surrounding the elastic sleeve.

3. The tourniquet according to claim 1, wherein the first portion is capable of taking on an annular shape extending round an axis in the deployed configuration, and is manufactured in a non-extendable material parallel to the axis.

4. The tourniquet according to claim 1, wherein the drive element comprises a second portion continuing the first portion and wherein, in the folded configuration, the second portion is folded over the first portion so as to form, between the first and second portion of the drive element, a cavity for housing the elastic sleeve held in the stretched position.

5. The tourniquet according to the claim 4, also comprising means for locking the second portion of the drive element in the folded position on the first portion of the drive element.

6. The tourniquet according to claim 5, wherein the locking means comprise:
at least one opening formed in the first portion,
at least one opening formed in the second portion,
a cord capable of being passed through the two openings, the cord having a free end portion capable of being accessible from the exterior of the tourniquet and of being pulled manually to withdraw the cord out of the openings, so as to unlock the two portions from one another.

7. The tourniquet according to claim 6, wherein the openings are disposed with respect to one another so that a portion of the cord extending from one of the openings to the other opening forms an abutment preventing the elastic sleeve housed in the cavity from leaving the cavity.

8. The tourniquet according to claim 4, wherein the drive element comprises a third portion which continues the second portion and which is also fixed to the grip element, the second portion extending between the elastic sleeve and the third portion in the folded configuration.

9. The tourniquet according to claim 1, wherein the displacement of the grip element inducing the driving, by the drive element of the elastic sleeve from the stretched position around the elastic sleeve to the constricting position, is a displacement caused by a manual pull exerted on the grip element along the limb.

10. The tourniquet according to claim 1, wherein
the grip element comprises a fastening element capable of fastening the grip element removably to a piece of clothing while the elastic sleeve is held around the support in the stretched position, and
the grip element is fastened to the drive element to prevent, when the grip element is attached to the piece of clothing, the driving, by the driving element, of the elastic sleeve from the stretched position around the support to the constricting position.

11. The tourniquet according to claim 10, wherein the fastening element is capable of forming, with another fastening element, a hook-and-pile connection.

12. The tourniquet according to claim 10, wherein the fastening element is capable of fastening the grip element to a portion of a piece of clothing surrounding a third portion of the limb when the support surrounds the first portion of the limb, the second and third portions of the limb being situated on either side of the first portion of the limb.

13. The tourniquet according to claim 10, wherein the grip element comprises a flap movable with respect to the drive member between:
an unfolded configuration wherein the fastening element faces the piece of clothing, so as to be able to be fastened to the piece of clothing,
a configuration folded back over the drive element in the direction of the constricting position.

14. The tourniquet according to claim 1, wherein the support has an internal surface capable of being oriented toward the first portion of the limb, and an external surface opposite to the internal surface, the tourniquet also comprising:
an internal textile element covering the internal surface, and/or
an external textile element covering the external surface.

15. The tourniquet according to claim 14, wherein the internal textile element and the external textile element together define a pocket for containing the support, the pocket being provided with an opening by which the support is capable of being withdrawn from the pocket.

16. The tourniquet according to claim 15, also comprising means for blocking the opening of the pocket.

17. The tourniquet according to claim 15, wherein at least one of the textile elements is formed starting with a strip having two opposite free edges brought to face one another without overlapping them, and sewn to one another by means of a topstitch.

18. The tourniquet according to claim 17, wherein the strip has the shape of a parallelogram.

19. The tourniquet according to claim 1, wherein the elastic sleeve has, at rest, an annular shape extending around an axis, and comprises at least one elastic compression yarn arranged so as to follow a substantially helical trajectory around and along the axis.

20. A piece of clothing or portion of a piece of clothing comprising at least one tourniquet according to claim 1.

* * * * *